United States Patent
Sharma et al.

(10) Patent No.: US 6,355,853 B1
(45) Date of Patent: Mar. 12, 2002

(54) SELECTIVE XYLENES ISOMERIZATION AND ETHYLBENZENE CONVERSION

(75) Inventors: Sanjay B. Sharma, Burr Ridge; Sergey V. Gurevich, Chicago, both of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/511,936

(22) Filed: Feb. 24, 2000

(51) Int. Cl.$^7$ ................ C07C 5/27; C07C 5/29
(52) U.S. Cl. ....................... 585/481; 585/482
(58) Field of Search ................. 585/481, 482, 585/480, 477; 502/77, 74, 66, 64, 71

(56) References Cited

U.S. PATENT DOCUMENTS

| | | | |
|---|---|---|---|
| 3,856,872 A | 12/1974 | Morrison | 260/668 A |
| 4,101,598 A * | 7/1978 | Whittam et al. | 260/668 A |
| 4,537,866 A * | 8/1985 | Gilson | 502/70 |
| 4,626,609 A | 12/1986 | Shihabi | 585/467 |
| 4,724,066 A * | 2/1988 | Kirker et al. | 208/114 |
| 4,727,209 A * | 2/1988 | Chao | 585/466 |
| 4,899,012 A | 2/1990 | Sachtler et al. | 585/482 |

* cited by examiner

*Primary Examiner*—Thuan D. Dang
(74) *Attorney, Agent, or Firm*—John G. Tolomei; John F. Spears, Jr.

(57) ABSTRACT

This invention is drawn to a process for isomerizing a non-equilibrium mixture of xylenes and ethylbenzene using a catalyst comprising a zeolite, a platinum-group metal and a silica binder, resulting in a greater yield of para-xylene at favorable conditions compared to processes of the known art.

3 Claims, 2 Drawing Sheets

SELECTIVE XYLENES ISOMERIZATION AND ETHYLBENZENE CONVERSION

FIELD OF THE INVENTION

This invention relates to catalytic hydrocarbon conversion, and more specifically a process for aromatics isomerization.

GENERAL BACKGROUND AND RELATED ART

The xylenes, para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production.

Xylene isomers from catalytic reforming or other sources generally do not match demand proportions as chemical intermediates, and further comprise ethylbenzene which is difficult to separate or to convert. Para-xylene in particular is a major chemical intermediate with rapidly growing demand, but amounts to only 20–25% of a typical $C_8$-aromatics stream. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers which is lean in the desired xylene isomer to a mixture which approaches equilibrium concentrations.

Various catalysts and processes have been developed to effect xylene isomerization. In selecting appropriate technology, it is desirable to run the isomerization process as close to equilibrium as practical in order to maximize the para-xylene yield; however, associated with this is a greater cyclic $C_8$ loss due to side reactions. The approach to equilibrium that is used is an optimized compromise between high $C_8$ cyclic loss at high conversion (i.e. very close approach to equilibrium) and high utility costs due to the large recycle rate of unconverted $C_8$ aromatics.

Catalysts for isomerization of $C_8$ aromatics ordinarily are classified by the manner of processing ethylbenzene associated with the xylene isomers. Ethylbenzene is not easily isomerized to xylenes, but it normally is converted in the isomerization unit because separation from the xylenes by superfractionation or adsorption is very expensive. One approach is to react the ethylbenzene to form a xylene mixture via conversion to and reconversion from naphthenes in the presence of a solid acid catalyst with a hydrogenation-dehydrogenation function. An alternative widely used approach is to dealkylate ethylbenzene to form principally benzene while isomerizing xylenes to a near-equilibrium mixture. The former approach enhances xylene yield by forming xylenes from ethylbenzene, while the latter approach commonly results in higher ethylbenzene conversion, thus lowering the quantity of recycle to the para-xylene recovery unit and concomitant processing costs.

In the past twenty years or so, crystalline aluminosilicate zeolite-containing catalysts have become prominent for xylene isomerization. U.S. Pat. No. 3,856,872 (Morrison), for example, teaches xylene isomerization and ethylbenzene conversion with a catalyst containing ZSM-5, -12, or -21 zeolite. U.S. Pat. No. 4,626,609 (Shihabi) discloses conversion of xylene isomers using a catalyst comprising a composite which has been steamed at 200° to 500° C. U.S. Pat. No. 4,899,012 (Sachtler et al.) teaches the use of a catalyst containing lead, a Group VIII metal, a pentasil zeolite and an inorganic-oxide binder to isomerize xylenes and dealkylate ethylbenzene. Development efforts continue toward realizing economically attractive isomerization catalysts with a superior combination of activity, selectivity and stability.

SUMMARY OF THE INVENTION

A principal object of the present invention is to provide a novel isomerization process for alkylaromatic hydrocarbons. More specifically, this invention is directed to the processing of $C_8$ aromatics to increase the concentration of a desired xylene isomer.

This invention is based on the discovery that improved conversion of $C_8$ aromatics and selectivity for xylene isomerization can be obtained using a silica-bound zeolitic catalyst which has been prepared in a manner to achieve specified characteristics.

Accordingly, a broad embodiment of the invention is directed toward an alkylaromatics-isomerization process using a catalyst comprising a zeolitic aluminosilicate having a pore diameter of from about 5 to 8 Å, a platinum-group metal component and a silica binder. The process comprises isomerization preferably of a feedstock comprising a non-equilibrium mixture of xylenes and ethylbenzene at isomerization conditions to obtain a product having an increased para-xylene content relative to that of the feedstock. Relevant isomerization conditions comprise a temperature of from about 300° to 600° C., a pressure of from about 100 kPa to 5 MPa, a mass hourly space velocity of from about 0.5 to 100 $hr^{-1}$. Operation at a temperature of between 370° to 500° C. at a mass hourly space velocity of from about 10 to 50 $hr^{-1}$ is especially favored. MFI-type zeolite is the favored zeolitic aluminosilicate, especially as contained in an oil-dropped spherical catalyst The catalyst has a low 4.6 torr water capacity of less than about 7 mass-%, and preferably between about 3 and about 5 mass-%. The platinum-group metal preferably comprises platinum in a low concentration of between 100 and 2000 mass-ppm, and more preferably between about 200 and 800 mass-ppm, of the catalyst. The finished catalyst optimally has a water capacity at 4.6 torr and 25° C. of no more than about 5.5 mass-%

These, as well as other objects and embodiments, will become evident from the following detailed description of the invention.

DETAILED DESCRIPTION OF THE INVENTION

Figure 1:
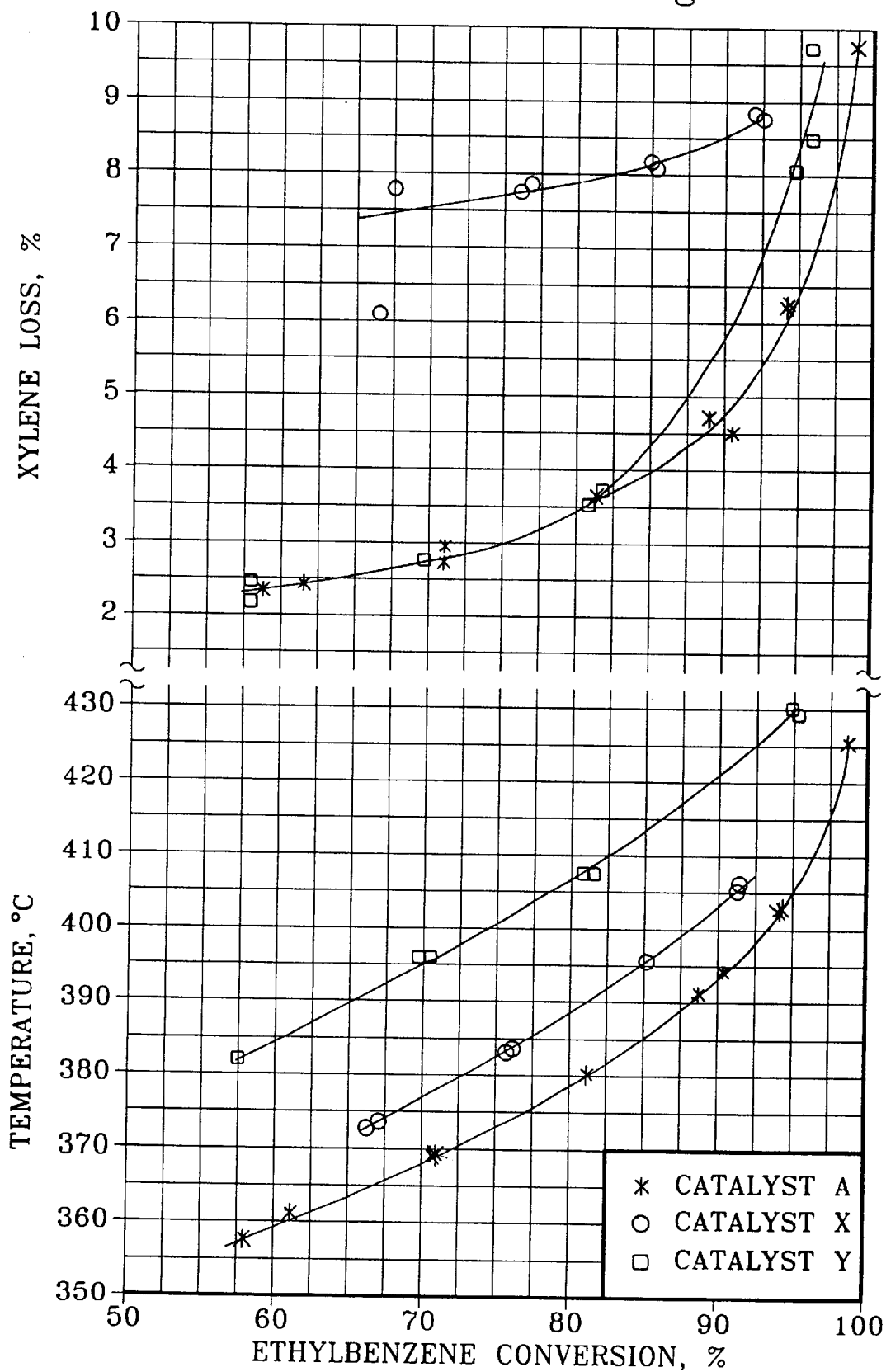
FIG. 1 shows relative activity and selectivity, in terms of process xylenes losses, of catalysts of the invention and the known art.

The feedstock to aromatics isomerization comprises isomerizable alkylaromatic hydrocarbons of the general formula $C_6H_{(6-n)}R_n$, where n is an integer from 1 to 5 and R is $CH_3$, $C_2H_5$, $C_3H_7$, or $C_4H_9$, in any combination and including all the isomers thereof to obtain more valuable isomers of the alkylaromatic. Suitable alkylaromatic hydrocarbons include, for example but without so limiting the invention, ortho-xylene, meta-xylene, para-xylene, ethylbenzene, ethyltoluenes, trimethylbenzenes, propylbenzenes, ethyldimethyl-benzenes, diethylbenzenes, methylpropylbenzenes, ethylpropylbenzenes, triethylbenzenes, di-isopropyl-benzenes, and mixtures thereof.

Isomerization of a $C_8$-aromatic mixture containing ethylbenzene and xylenes is a particularly preferred application of the invention. Generally such a mixture will have an ethylbenzene content in the approximate range of 5 to 50 mass-%, an ortho-xylene content in the approximate range of 0 to 35 mass-%, a meta-xylene content in the approximate range of 20 to 95 mass-% and a para-xylene content in the approximate range of 0 to 15 mass-%. It is preferred that the aforementioned $C_8$ aromatics comprise a non-equilibrium mixture, i.e., at least one $C_9$-aromatic isomer is present in a concentration that differs substantially from the equilibrium concentration at isomerization conditions. Usually the non-equilibrium mixture is prepared by removal of para- and/or ortho-xylene from a fresh $C_8$-aromatics feed obtained from processes, such as catalytic reforming and/or extraction, for the production and recovery of aromatics from other hydrocarbons.

The alkylaromatic hydrocarbons may be utilized in the present invention as found in appropriate fractions from various refinery petroleum streams, e.g., as individual components or as certain boiling-range fractions obtained by the selective fractionation and distillation of catalytically cracked or reformed hydrocarbons. The isomerizable aromatic hydrocarbons need not be concentrated; the process of this invention allows the isomerization of alkylaromatic-containing streams such as catalytic reformate with or without subsequent aromatics extraction to produce specified xylene isomers and particularly to produce para-xylene. A $C_8$-aromatics feed to the present process may contain nonaromatic hydrocarbons, i.e., naphthenes and paraffins, in an amount up to 30 mass-%. Preferably the isomerizable hydrocarbons consist essentially of aromatics, however, to ensure pure products from downstream recovery processes.

According to the process of the present invention, an alkylaromatic hydrocarbon feed mixture, preferably in admixture with hydrogen, is contacted with a catalyst of the type hereinafter described in an alkylaromatic hydrocarbon isomerization zone. Contacting may be effected using the catalyst in a fixed-bed system, a moving-bed system, a fluidized-bed system, or in a batch-type operation. In view of the danger of attrition loss of the valuable catalyst and of the simpler operation, it is preferred to use a fixed-bed system. In this system, a hydrogen-rich gas and the feed mixture are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone.

The reactants may be contacted with the catalyst bed in either upward-, downward-, or radial-flow fashion, and the reactants may be in the liquid phase, a mixed liquid-vapor phase, or a vapor phase when contacted with the catalyst.

The alkylaromatic feed mixture, preferably a non-equilibrium mixture of $C_8$ aromatics, is contacted with the isomerization catalyst at suitable alkylaromatic-isomerization conditions. Such conditions comprise a temperature ranging from about 100° to 600° C. or more, and preferably is in the range of from about 370° to 500° C. The pressure generally is from about 100 kPa to 10 MPa, and more usually no more than about 5 MPa. Sufficient catalyst is contained in the isomerization zone to provide a mass hourly space velocity with respect to the hydrocarbon feed mixture of from about 0.5 to 100 $hr^{-1}$, and preferably 2 to 50 $hr^{-1}$; favorable results have been obtained at mass hourly space velocities of at least about 10 $hr^{-1}$ and higher. The hydrocarbon feed mixture optimally is reacted in admixture with hydrogen at a hydrogen/hydrocarbon mole ratio of about 0.5:1 to about 10:1 or more; other inert diluents such as nitrogen, argon and light hydrocarbons may be present.

The particular scheme employed to recover an isomerized product from the effluent of the reactors of the isomerization zone is not deemed to be critical to the instant invention, and any effective recovery scheme known in the art may be used. Typically, the reactor effluent is condensed and the hydrogen and light-hydrocarbon components removed therefrom by flash separation. The condensed liquid product then is fractionated to remove light and/or heavy byproducts and obtain the isomerized product. In some instances, certain product species such as ortho-xylene may be recovered from the isomerized product, alone or in combination with the fresh $C_8$ aromatics feed, by selective fractionation. The product from isomerization of $C_8$ aromatics usually is processed to selectively recover the para-xylene isomer, optionally by crystallization, alone or in combination with the fresh $C_8$ aromatics feed. Selective adsorption is preferred using crystalline aluminosilicates according to U.S. Pat. No. 3,201,491. Improvements and alternatives within the preferred adsorption recovery process are described in U.S. Pat. Nos. 3,626,020; 3,696,107; 4,039,599; 4,184,943; 4,381,419 and 4,402,832; incorporated herein by reference thereto.

In a separation/isomerization process combination relating to the processing of an ethylbenzene/xylene mixture, a fresh $C_8$-aromatics feed is combined with isomerized product comprising $C_8$ aromatics and naphthenes from the isomerization reaction zone and fed to a para-xylene separation zone from which pure para-xylene is recovered. The para-xylene-depleted stream from the separation zone, comprising a non-equilibrium mixture of $C_8$ aromatics, comprising xylenes and ethylbenzene, is fed to the isomerization reaction zone, where the $C_8$-aromatic isomers are isomerized to near-equilibrium levels to obtain the isomerized product. In this process scheme non-recovered $C_8$-aromatic isomers preferably are recycled to extinction until they are either converted to para-xylene or lost due to side-reactions. Ortho-xylene separation, preferably by fractionation, also may be effected on the fresh $C_8$-aromatic feed or isomerized product, or both in combination, preferably prior to para-xylene separation.

The isomerization catalyst of the present invention comprises a molecular sieve and a refractory inorganic oxide. The preferred molecular sieves are zeolitic alumino-silicates selected from those which have a Si:$Al_2$ ratio greater than about 10, preferably greater than 20, and a pore diameter of about 5 to 8 Angstroms (Å). Specific examples of suitable zeolites are the MFI, MEL, EUO, FER, MFS, MTT, MTW, TON, MOR and FAU types of zeolites. Pentasil zeolites MFI, MEL, MTW and TON are preferred, and MFI-type zeolites, often designated ZSM-5, are especially preferred.

The preparation of the preferred MFI-type zeolites by crystallizing a mixture comprising an alumina source, a silica source and an alkali metal source is well known in the art. Conversion of an alkali-metal-form zeolite to the hydrogen form may be performed by treatment with an aqueous solution of a mineral acid. Alternatively, hydrogen ions can be incorporated into the pentasil by ion exchange with ammonium salts such as ammonium hydroxide or ammonium nitrate followed by calcination.

The relative proportion of zeolite in the catalyst may range from about 10 to about 99 mass-%, with about 20 to about 90 mass-% being preferred. There is a tradeoff between the zeolite content of the catalyst composite and the pressure, temperature and space velocity of an isomerization operation in maintaining low xylene losses.

A refractory binder or matrix is utilized to facilitate fabrication of the isomerization catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria and silica. Alumina and/or silica are preferred binder components. The catalyst also may contain, without so limiting the composite, one or more of (1) other inorganic oxides including, but not limited to, beryllia, germania, vanadia, tin oxide, zinc oxide, iron oxide and cobalt oxide; (2) non-zeolitic molecular sieves, such as the aluminophosphates of U.S. Pat. No. 4,310,440, the silicoaluminophosphates of U.S. Pat. No. 4,440,871 and ELAPSOs of U.S. Pat. No. 4,793,984; and (3) spinels such as $MgAl_2O_4$, $FeAl_2O_4$, $ZnAl_2O_4$, $CaAl_2O_4$, and other like compounds having the formula $MO\text{---}Al_2O_3$ where M is a metal having a valence of 2; which components can be added to the composite at any suitable point.

A preferred binder is a form of amorphous silica. An especially preferred amorphous silica is a synthetic, white, amorphous silica (silicon dioxide) powder which is classed as wet-process, hydrated silica. This type of silica is produced by a chemical reaction in a water solution, from which it is precipitated as ultra-fine, spherical particles. It is preferred that the BET surface area of the silica is in the range from about 300–800 $m^2/g$.

A preferred shape for the catalyst composite is an extrudate. The well-known extrusion method initially involves mixing of the molecular sieve, either before or after adding metallic components, with the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with a moisture content in the range of from 30 to 50 wt. % being preferred. The dough then is extruded through a die pieced with multiple holes and the spaghetti-shaped extrudate is cut to form particles in accordance with techniques well known in the art. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

The alternative oil-drop method of preparing the catalyst involves the gelation of a silica hydrosol using the oil-drop method. One method of gelling this mixture involves combining a gelling agent with the mixture and then dispersing the resultant combined mixture into an oil bath or tower which has been heated to elevated temperatures such that gelation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 100° to 150° C. and subjected to a calcination procedure at a temperature of about 450° to 700° C. for a period of about 1 to 20 hours.

The combined mixture preferably is dispersed into the oil bath in the form of droplets from a nozzle, orifice or rotating disk. Alternatively, the particles may be formed by spray-drying of the mixture at a temperature of from about 425° to 760° C. In any event, conditions and equipment should be selected to obtain small spherical particles; the particles preferably should have an average diameter of less than about 1.0 mm, more preferably from about 0.2 to 0.8 mm, and optimally from about 0.3 to 0.8 mm.

The catalyst of the present invention may contain a halogen component, comprising either fluorine, chlorine, bromine or iodine or mixtures thereof, with chlorine being preferred. Preferably, however, the catalyst contains no added halogen other than that associated with other catalyst components.

The catalyst composite is dried at a temperature of from about 100° to about 320° C. for a period of from about 2 to about 24 or more hours and, usually, calcined at a temperature of from 400° to about 650° C. in an air atmosphere for a period of from about 0.1 to about 10 hours until the metallic compounds present are converted substantially to the oxide form. If desired, the optional halogen component may be adjusted by including a halogen or halogen-containing compound in the air atmosphere.

The catalytic composite optimally is subjected to steaming to tailor its acid activity. The steaming may be effected at any stage of the zeolite treatment, but usually is carried out on the composite of zeolite binder prior to incorporation of the platinum-group metal. Steaming conditions comprise a water concentration of about 5 to 100 volume-%, pressure of from about 100 kPa to 2 MPa, and temperature of between about 600° and 1200° C.; the steaming temperature preferably between about 650° and 1000° C., more preferably at least about 750° C. and optionally may be about 775° C. or higher. In some cases, temperatures of about 800° to 850° C. or more may be employed. The steaming should be carried out for a period of at least one hour, and periods of 6 to 48 hours are preferred.

Alternatively or in addition to the steaming, the composite may be washed with one or more of a solution of ammonium nitrate, a mineral acid, and/or water. Considering the first alternative, the catalyst may be washed with a solution of about 5 to 30 mass-% ammonium nitrate. When acid washing is employed, a mineral acid such as HCl or $HNO_3$ is preferred; sufficient acid is added to maintain a pH of from more than 1 to about 6, preferably from about 1.5 to 4. The catalyst is maintained in a bed over which the solution and/or water is circulated for a period of from about 0.5 to 48 hours, and preferably from about 1 to 24 hours. The washing may be effected at any stage of the preparation, and two or more stages of washing may be employed.

Prior to addition of the platinum-group metal component the composite preferably is ion-exchanged with a salt solution containing at least one hydrogen-forming cation such as $NH_4^+$ or quaternary ammonium. The hydrogen-forming cation replaces principally alkali-metal cations to provide, after calcination, the hydrogen form of the zeolite component.

A platinum-group metal, including one or more of platinum, palladium, rhodium, ruthenium, osmium, and iridium, is an essential component of the present catalyst. The preferred platinum-group metals are platinum and palladium, with platinum being especially preferred. The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all of the platinum-group metal component exists in a reduced state. The platinum-group metal component generally comprises from about 10 to about 10,000 mass-ppm (parts per million) of the final catalyst composite, calculated on an elemental basis, with a level of about 100 to about 2000 mass-ppm being particularly suitable. When using a platinum component, very low levels of about 200 to 800 mass-ppm of platinum on the catalyst, on an elemental basis, are favored; levels of less than about 600 mass-ppm are especially favored and levels of about 300 to about 500 mass-ppm show excellent results. When using a palladium component, levels of about 400 to 2000 mass-ppm of palladium on the catalyst, on an elemental basis, are favored and levels of between about 500 and 1200 mass-ppm are especially favored.

The platinum-group metal component may be incorporated into the catalyst composite in any suitable manner. One method of preparing the catalyst involves the utilization of a water-soluble, decomposable compound of a platinum-group metal to impregnate the calcined sieve/binder composite. Alternatively, a platinum-group metal compound may be added at the time of compositing the sieve component and binder. Yet another method of effecting a suitable metal distribution is by compositing the metal component with the binder prior to co-extruding the sieve and binder. Complexes of platinum-group metals which may be employed according to the above or other known methods include chloroplatinic acid, chloropalladic acid, ammonium chloroplatinate, bromoplatinic acid, platinum trichloride, platinum tetrachloride hydrate, platinum dichlorocarbonyl dichloride, tetraamineplatinum chloride, dinitrodiaminoplatinum, sodium tetranitroplatinate (II), palladium chloride, palladium nitrate, palladium sulfate, diaminepalladium (II) hydroxide, tetraaminepalladium (II) chloride, and the like.

It is within the scope of the present invention that the catalyst may contain other metal components known to modify the effect of the platinum-group metal component. Such metal modifiers may include without so limiting the invention rhenium, tin, germanium, lead, cobalt, nickel, indium, gallium, zinc, and mixtures thereof. Catalytically effective amounts of such metal modifiers may be incorporated into the catalyst by any means known in the art to effect a homogeneous or stratified distribution.

After addition of the metal component, the resultant catalytic composite usually is dried at a temperature of about 100° to about 320° C. for a period of from about 1 to about 24 or more hours. The dried composite then is calcined at a temperature of from about 400° to about 600° C. in an air atmosphere for a period of from about 0.1 to 10 hours to convert the metallic components substantially to the oxide form.

The calcined composite optimally is subjected to a substantially water-free reduction step to insure a uniform and finely divided dispersion of the optional metallic components. The reduction optionally may be effected on the catalyst as loaded in the isomerization-process reactor of the present invention prior to the startup of the isomerization process. Substantially pure and dry hydrogen (i.e., less than 20 vol. ppm $H_2O$) preferably is used as the reducing agent in this step. The reducing agent contacts the catalyst at conditions, including a temperature of from about 200° to about 650° C. and for a period of is from about 0.5 to about 10 hours, effective to reduce substantially all of the Group VIII metal component to the metallic state. In some cases the resulting reduced catalyst composite may also be beneficially subjected to presulfiding by a method known in the art to incorporate in the catalyst composite from about 0.01 to about 0.5 mass-% sulfur, calculated on an elemental basis, into the catalyst.

The finished catalyst has a McBain water capacity at 4.6 torr of between about 2 and 7 mass-%, preferably between about 3.0 and about 5.0 mass-%, and with the usual optimum being between about 3.5 and 4.5 mass-%. Water capacity may be measured by the following procedure:

Activation Step

Empty-pails readings (W1) are taken, then the catalyst is activated in vacuum for about 16 hours overnight at 375° to 400° C.; the vacuum of the system should be less than 1 millitorr. The catalyst is cooled to room temperature and the McBain tubes containing the activated catalyst are closed off; a room-temperature reading (W2) of the activated catalyst then is taken. An ice bath then is assembled around the water reservoir so that the water is maintained at 0° C. during the adsorption step Adsorption Step The manifold is purged of water vapor by opening the water reservoir; the mercury U-type manometer should read a pressure of 4.6 torr. Open the tubes and record the adsorption starting time. The catalyst is allowed to equilibrate for at least 1.5 hours, the final time is recorded, and the reading (W3) is taken of the catalyst equilibrated with water vapor. The water capacity is calculated as:

$$\text{Capacity, mass-\%} = [(W2-W3)/(W1-W2)]*100$$

The gradual accumulation of coke and other deactivating carbonaceous deposits on the catalyst during the operation of the isomerization process will eventually reduce the activity and selectivity of the process to a level such that regeneration is desirable. When the performance of the catalyst has decayed to the point where it is desired to regenerate the catalyst, the introduction of the hydrocarbon charge stock into the conversion zone containing the catalyst is stopped and the conversion zone purged with a suitable gas stream. Any suitable regeneration method may be used to restore catalyst activity and selectivity, either in situ or by unloading and regenerating the catalyst in an off-line facility.

In one suitable regeneration method, the first step is a carbon-burn step. The carbon-burn step involves contacting the deactivated catalyst with a gaseous mixture of oxygen in a concentration ranging from 0.1 to 21 mole-% or higher and an inert gas. Levels of oxygen higher than 21 mole-% may be effected by supplying oxygen in pure form from cylinders or by other means. Typical inert gases useful in the carbon-burn step include nitrogen, helium, carbon dioxide, and the like gases or mixtures thereof. Preferably the oxygen level of the regeneration gas is slowly increased during the carbon-burn step based upon the increase in temperature of the regeneration gas as it passes across the catalyst bed.

The carbon burn generally is effected at a temperature of from about 350° to 600° C. The pressure is sufficient to maintain flow through the zone containing the deactivated catalyst, typically between 100 kPa to 4 MPa, at a gas hourly space velocity of about 100 to about 25,000 $hr^{-1}$. The carbon-burn step ordinarily is terminated when the differential temperature across the zone containing the catalyst is about zero for a period of about 0.5 to 6 hours.

A halogen or halogen-containing compound or a mixture thereof usually is added to the regeneration gas at any stage of or following the carbon-burn step. The halogen or halogen-containing compound is typically added to the regeneration gas such that the regeneration gas contains from 0.005 to about 5 mole percent of a halogen or halogen-containing compound. Although a halogen gas such as chlorine, fluorine, or bromine may be used for this purpose, it is generally more convenient to employ a halogen-containing compound such as an alkylhalide, which upon exposure to the conditions utilized in these steps is decomposed to form the corresponding hydrogen halide.

The regenerated catalyst typically is purged with nitrogen or another inert gas to displace oxygen and until effluent gases from the catalyst are substantially free of oxygen and water. The purged catalyst is cooled and purged once again with hydrogen to commence a reduction step. In the reduction step, the catalyst is contacted with a hydrogen stream (preferably water-free) at a temperature of about 300° to 600° C. for a period of about 0.5 to 6 hours. The pressure and gas rates utilized for this step preferably correspond to those reported in conjunction with the discussion of the carbon-burn step. The reduction step reduces metallic components essentially to an elemental state to produce regenerated catalyst having activity, selectivity, and stability characteristics comparable to those possessed initially by the fresh catalyst.

EXAMPLES

The following examples are presented only to illustrate certain specific embodiments of the invention, and should not be construed to limit the scope of the invention as set forth in the claims. There are many possible other variations, as those of ordinary skill in the art will recognize, which are within the spirit of the invention.

Example I

A silica-bound MFI catalyst was prepared to illustrate the transalkylation process of the invention. Ammonia-exchanged MFI-type zeolite having an $Si/Al_2$ ratio of about 38 was blended with Methocel in a muller. Hydrated amorphous silica powder, Ludox AS-40, was added in proportion to effect a final catalyst MFI content of about 67 mass-%. The mixture and sufficient deionized water to effect an extrudable dough having a moisture content of about 40 mass-% was blended thoroughly in the muller. The dough then was extruded through a cylindrical die to form cylindrical extrudates having a diameter of about 1.6 mm. The extrudates then were water washed, air dried, and calcined at a temperature of about 550° C. and then subjected to steaming at a temperature of about 660° C. in an atmosphere of 40% steam in air for 12 hours.

The steamed extrudates then were column-washed with ammonium nitrate at 88° C. for 5 hours, then washed with deionized water and dried at 510° C. for about 9 hours. The dried extrudates were metal-impregnated by rolling in a solution of chloroplatinic acid at temperatures of 60–100° C. for 6–7 hours. Upon completion of the impregnation, the composite was dried oxidized, and reduced to yield a catalyst, utilized to illustrate the process of the invention, was designated as Catalyst A.

Example II

An alumina-bound catalyst was prepared as a control for comparison of isomerization results with Catalyst A. A first solution of aluminum nitrate was prepared to which was added a second solution of $NH_4OH$. The second solution was added slowly maintaining the pH of the first solution at 8 until gellation of the aluminum occurred. The hydrogel of alumina was slurried with water and filtered to obtain a filter cake having a moisture content of approximately 90 wt. %. A portion of this filter cake was dried at 150° C. to a moisture content of about 60 wt. %. This dried material was then ground to produce powdered alumina.

An extrudable dough was prepared by combining and mixing about 67 mass-% MFI zeolite with hydrogel alumina and powdered alumina. The dough then was extruded to form cylindrical extrudates. The extrudates were directly subjected to calcination in flowing air at a temperature of about 600° C.

The calcined extrudates were then subjected to an impregnation procedure using a solution of tetraamine platinum chloride. The catalyst then was dried, oxidized, and reduced to yield a catalyst containing about 400 mass-ppm platinum. This reference catalyst is designated Catalyst X.

Example III

A second control catalyst was prepared for comparison with the catalyst of the invention. This catalyst consisted essentially of approximately 11 mass-% hydrogen-form ZSM-5 zeolite and 0.29 mass-% platinum, with the remainder being alumina binder. MFI zeolite was added to an alumina sol solution, prepared by digesting metallic aluminum in hydrochloric acid, in an amount sufficient to yield a zeolite content in the finished catalyst of about 11 mass-%. A second solution of hexamethylenetetramine (HMT) was prepared and added to the zeolite/alumina sol mixture to give homogeneous admixture. This admixture was then dispersed as droplets into an oil bath maintained at about 93° C. The droplets remained in the oil bath at 150° C. until they set and formed hydrogel spheres. These spheres were removed from the oil bath, water washed with a 0.5% ammonia/water solution, air dried, and calcined at a temperature of about 650° C. These calcined spheres were then is coimpregnated with a solution of chloroplatinic acid, lead as $Pb(NO_3)_2$ and hydrochloric acid to yield about 0.2 mass-% platinum and 0.8 mass-% lead on the finished catalyst. The impregnated spheres were oxidized, subjected to a reducing environment of $H_2$ at 565° C., and sulfided with $H_2S$. This catalyst of the known art was designated Catalyst Y.

Example IV

The comparative isomerization performance of the catalyst of the invention and the control catalysts were evaluated using a pilot plant processing non-equilibrium $C_8$-aromatic feed having the following composition in mol-%:

| | |
|---|---|
| ethylbenzene | 7.3–7.4% |
| para-xylene | 0.1% |
| meta-xylene | 70.8–71.3% |
| ortho-xylene | 21.3–21.8% |

This feed was isomerized at a pressure of a pressure of 1.3 MPa, a mass hourly space velocity of 10 $hr^{-1}$, and a hydrogen/hydrocarbon mole ratio of 4. Reactor temperature was adjusted to effect a range of conversion levels, expressed as the disappearance per pass of ethylbenzene. Ethylbenzene, plus the small amount of xylene loss, is converted primarily to benzene and toluene with smaller amounts of light gases. Results of the tests, comparing the loss of valuable xylenes, may be summarized as follows at 65% ethylbenzene conversion:

| Catalyst: | A | X | Y |
|---|---|---|---|
| Temperature, ° C. | 364 | 372 | 391 |
| Product para-xylene/xylenes, % | 23.7 | 23.8 | 24.0 |
| Xylenes loss, % | 2.6 | 7.4 | 2.6 |

Catalyst A of the invention demonstrated exceptional activity, as evidenced by the low temperature required to achieve 65% ethylbenzene conversion, along with low xylene losses in comparison to catalysts of the known art. The relative performance of the three catalysts, indicating xylene losses and activity as a function of conversion, is shown in FIG. 1.

Example V

The effect of steaming temperature on catalyst properties and performance was studied by preparing and testing a series of catalysts having a neutral binder. Calcined spheres having a zeolite content of about 67 mass-% were prepared and steamed as follows. a homogeneous admixture of HMT, phosphorus, alumina sol, and zeolite was dispersed as droplets into an oil bath maintained at about 93° C. The droplets remained in the oil bath until they set and formed hydrogel spheres having a diameter of about 1.6 mm. The spheres were removed from the oil bath, water washed, air dried, and calcined at a temperature of about 550° C. The calcined spheres then were subjected to steaming either by ramping to the temperature indicated ("ramp") or by immediately subjecting the catalyst to the temperature ("flat"). The spheres then were impregnated to effect a platinum content of the catalyst of 420–460 mass-ppm, dried, oxidized and reduced. The finished catalysts had 4.6 torr water capacities in mass-%, as measured by the previously described McBain water-capacity test, as indicated below:

| Catalyst | Steaming Temp., ° C. | Water Capacity |
|---|---|---|
| A | 660 ramp | 5.02 |
| B | 705 ramp | 6.01 |
| C | 732 ramp | 5.44 |
| D | 760 ramp | 5.26 |
| E | 788 ramp | 5.36 |
| F | 788 flat | 4.29 |

Example VI

The comparative isomerization performance of the catalysts of Example V was evaluated using a pilot plant processing non-equilibrium $C_8$-aromatic feed as described in Example IV. This feed was isomerized at a pressure of a pressure of 1.3 MPa, a mass hourly space velocity of 10 hr$^{-1}$, a hydrogen/hydrocarbon mole ratio of 4 and temperatures as shown below. Results of the tests may be summarized as follows at 65% ethylbenzene conversion:

| Catalyst | Temperature, ° C. | Xylene Loss |
|---|---|---|
| A | 392 | 1.5% |
| B | 357 | 2.7% |
| C | 363 | 2.5% |
| D | 363 | 2.0% |
| E | 357 | 3.3% |
| F | 382 | 1.4% |

Figure 2:
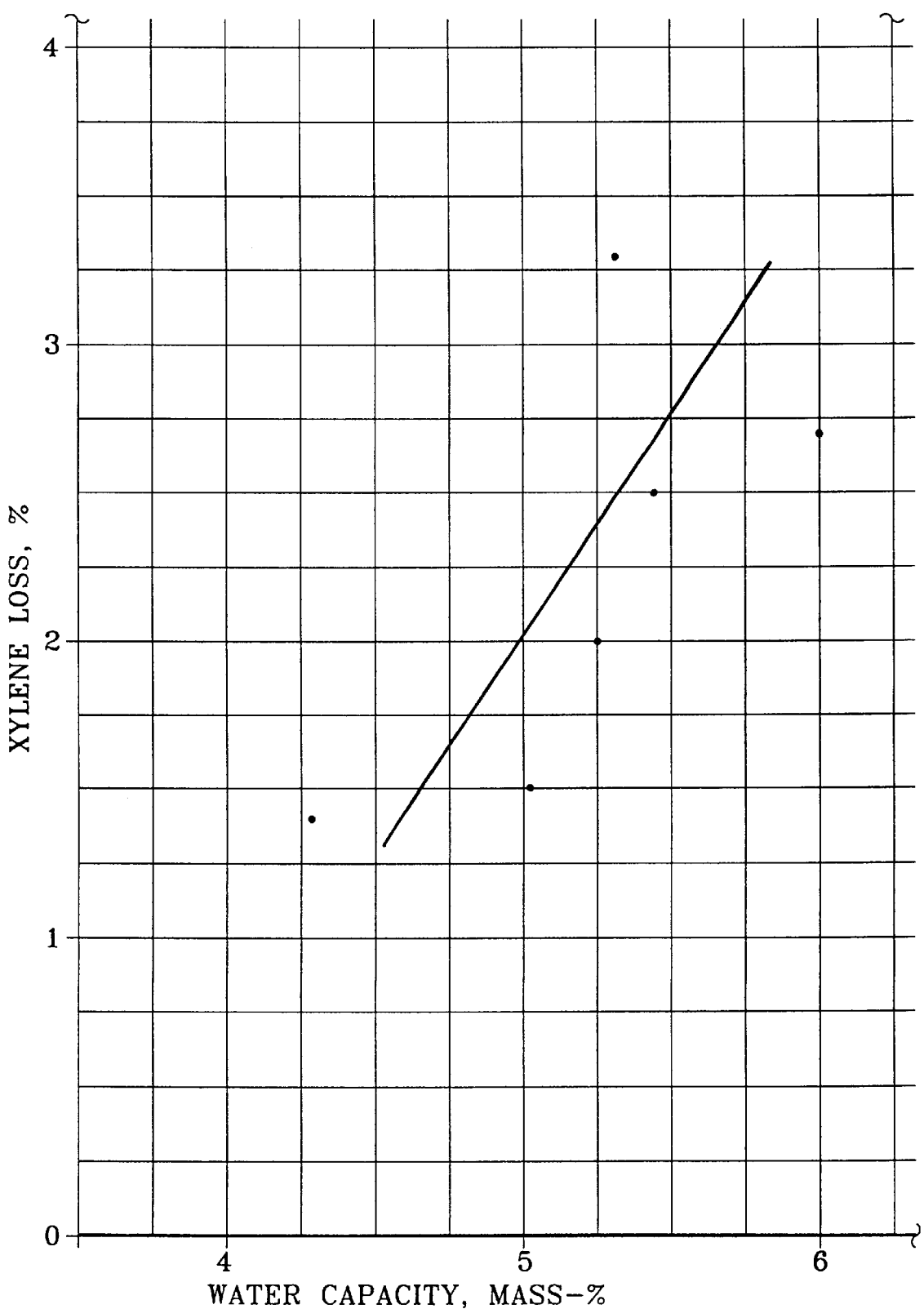
FIG. 2 shows process xylenes losses as a function of catalyst water capacity.

Reduced water capacity is a concomitant of catalyst activity, and xylene loss is low when this is achieved with high-temperature steaming without ramping. The results are shown graphically in FIG. 2.

Example VII

A further series of catalysts was prepared employing high steaming temperatures according to the invention, and performance was studied according to previously described testing procedures. Calcined spheres having a zeolite content of about 67 mass-% were prepared and steamed according to the procedure described in Example I. Steaming was effected in successive zones at temperatures of about 725° and 850° C. respectively. Catalysts O and Q were ammonium-exchanged. The spheres then were impregnated to effect a platinum content of the catalyst of 350–460 mass-ppm, dried, oxidized and reduced. The finished catalysts had 4.6 torr water capacities in mass-%, as measured by the previously described McBain water-capacity test, as indicated below: The comparative isomerization performance of the catalysts was evaluated using a pilot plant processing non-equilibrium $C_8$-aromatic feed as described in Example IV. This feed was isomerized at a pressure of a pressure of 1.3 MPa, a mass hourly space velocity of 10 hr$^{-1}$, a hydrogen/hydrocarbon mole ratio of 4 and a temperature as indicated below. Results of the tests were as follows:

| Catalyst | Water Capacity | Temp., ° C. | Ethylbenzene Conversion | Xylene Loss |
|---|---|---|---|---|
| L | 3.75 | 404 | 61.7% | 2.1% |
| M | 4.1 | 415 | 61.9% | 1.1% |
| N | 4.2 | 403 | 61.1% | 1.9% |
| O | 4.2 | 391 | 62.6% | 1.6% |
| P | 4.15 | 404 | 65.4% | 1.6% |
| Q | 4.15 | 393 | 67.2% | 1.3% |

We claim:
1. A process for the isomerization of a non-equilibrium feed mixture of xylenes and ethylbenzene comprising contacting the feed mixture in the presence of hydrogen with a catalyst having a 4.6 torr water capacity between 3 to 5 mass-%, consisting essentially of from about 10 to 99 mass-% of a MFI zeolitic aluminosilicate having a pore diameter of from 5 to 8 Å, from about 200 to 800 mass-ppm on an elemental basis of a platinum-group metal component, and the balance of a silica binder in an isomerization zone at isomerization conditions comprising a temperature of from about 370° C. to 500° C., a pressure of from 100 kPa to 5 Mpa, a mass hourly space velocity of from about 10 to 50 hr$^{-1}$ and a hydrogen-to-hydrocarbon mole ratio of from about 0.5:1 to 10:1 to obtain an isomerized product comprising a higher proportion of para-xylene than in the feed mixture.

2. The process of claim 1 wherein the 4.6 torr water capacity is between about 4.3 and 5.0 mass-%.

3. The process of claim 1 wherein the platinum-group metal component consisting essentially of less than 600 mass-ppm platinum on an elemental basis.

* * * * *